US010952902B2

(12) United States Patent
Hansson et al.

(10) Patent No.: US 10,952,902 B2
(45) Date of Patent: Mar. 23, 2021

(54) AUTOMATIC DARKENING FILTER ASSEMBLY FOR A WELDING PROTECTOR AND A WELDING PROTECTOR

(71) Applicant: 3M INNOVATIVE PROPERTIES COMPANY, St. Paul, MN (US)

(72) Inventors: Johan M. P. Hansson, Borlänge (SE); Kjell A. Hummel, BBorlänge (SE); Thomas B. Stenvall, Sundborn (SE); Linus P. Bastman, Orsa (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/348,576

(22) PCT Filed: Nov. 8, 2017

(86) PCT No.: PCT/US2017/060525
§ 371 (c)(1),
(2) Date: May 9, 2019

(87) PCT Pub. No.: WO2018/089415
PCT Pub. Date: May 17, 2018

(65) Prior Publication Data
US 2019/0262178 A1    Aug. 29, 2019

(30) Foreign Application Priority Data

Nov. 11, 2016 (EP) ...................................... 16198326

(51) Int. Cl.
*G02F 1/1333* (2006.01)
*A61F 9/06* (2006.01)
(Continued)

(52) U.S. Cl.
CPC ................ *A61F 9/067* (2013.01); *A61F 9/06* (2013.01); *G02B 7/00* (2013.01); *G02B 7/006* (2013.01); *G02F 1/133528* (2013.01)

(58) Field of Classification Search
CPC ....................................................... A61F 9/067
See application file for complete search history.

(56) References Cited

U.S. PATENT DOCUMENTS 3,344,434 A    10/1967  Beckmann
4,240,709 A    12/1980  Hornell
(Continued)

FOREIGN PATENT DOCUMENTS

CN          2062216 U      9/1990
CN        102508348 A      6/2012
(Continued)

OTHER PUBLICATIONS

International Search Report for PCT International Application No. PCT/US2017/060525, dated Feb. 16, 2018, 4 pages.
(Continued)

*Primary Examiner* — Sang V Nguyen
(74) *Attorney, Agent, or Firm* — Gregg H. Rosenblatt

(57) ABSTRACT

An automatic darkening filter assembly for a welding protector and a welding protector that includes the automatic darkening filter assembly. The automatic darkening filter assembly has a housing that forms an opening in which a switchable light filter is arranged. The switchable light filter is retained by a first and a second resilient gasket that are arranged on opposite sides of the switchable light filter and which each extend circumferentially adjacent a periphery of the switchable light filter. The invention helps maximizing the robustness of the welding protector and facilitates assembly.

17 Claims, 6 Drawing Sheets

(51) Int. Cl.
*G02B 7/00* (2021.01)
*G02F 1/1335* (2006.01)

(56) References Cited

U.S. PATENT DOCUMENTS

| | | | |
|---|---|---|---|
| 5,754,259 A | 5/1998 | Nakamatsu et al. | |
| 2013/0071303 A1* | 3/2013 | Macnamara | B01L 3/50857 422/500 |
| 2014/0007312 A1 | 1/2014 | Wright | |
| 2014/0168546 A1* | 6/2014 | Magnusson | A41D 13/1184 349/14 |
| 2016/0018316 A1* | 1/2016 | Rohrer | G01J 5/0875 359/511 |
| 2018/0355595 A1* | 12/2018 | Hillsten | E03C 1/264 |
| 2019/0091069 A1* | 3/2019 | Magnusson | A61F 9/061 |

FOREIGN PATENT DOCUMENTS

| | | | | |
|---|---|---|---|---|
| CN | 202870364 U | | 4/2013 | |
| JP | 2008-188802 | * | 8/2008 | B32B 27/30 |
| WO | WO 2012-037575 | | 3/2012 | |
| WO | WO 2014-092989 | | 6/2014 | |
| WO | WO 2015-034575 | | 3/2015 | |
| WO | WO 2017-196721 | | 11/2017 | |

OTHER PUBLICATIONS

Search Report for CN Appl. No. 201780069789.8, dated Jun. 22, 2020, 3 pp.

* cited by examiner

AUTOMATIC DARKENING FILTER ASSEMBLY FOR A WELDING PROTECTOR AND A WELDING PROTECTOR

CROSS REFERENCE TO RELATED APPLICATIONS

This application is a national stage filing under 35 U.S.C. 371 of PCT/US2017/060525, filed Nov. 8, 2017, which claims the benefit of European Application No. 16198326.7, filed Nov. 11, 2016, the disclosure of which is incorporated by reference in its/their entirety herein.

FIELD OF THE INVENTION

The invention relates to an automatic darkening filter assembly for a welding protector and a welding protector that includes the automatic darkening filter assembly. A two-part gasket is provided to hold a switchable light filter in place.

BACKGROUND ART

Automatic darkening filters commonly have a switchable filter that automatically changes from a light-transmission-state (or light-state) to a dark-transmission-state (or dark-state) in response to incident light. The switching is generally achieved through use of a photodetector that is located on, or as part of, personal protective equipment. The photodetector recognizes the presence of the incident light-to-be-filtered, and an electronic module generates a control voltage that, when applied to the switchable filter, causes the filter to change from the light-state to the dark-state.

Automatic light filters have been designed which contain liquid-crystal cells located between polarizing films. U.S. Pat. No. 4,240,709 to Hornell describes a switchable filter that has a single-twisted, nematic, liquid-crystal cell sandwiched between a pair of mutually crossed polarizers. The liquid-crystal cells are optically-transparent glass substrates that include transparent electrode and alignment layers. The liquid-crystal molecules orientate themselves in a particular direction when a voltage is applied across the liquid-crystal cell under the control of an electronic module. Many commercially available products use this kind of switchable filter.

The use of an automatic-darkening filter in a protective shield gives significant ergonomic benefits. Previously welders, for example, had to "nod" their welding shield down when they struck the welding arc to ensure that their eyes were protected from the torch light. Automatic welding filters eliminate this action since the welding shield can be left in position continuously.

SUMMARY OF THE INVENTION

The invention relates to an automatic darkening filter assembly for a welding protector. Further, the invention relates to a welding protector comprising the automatic darkening filter assembly of the invention.

A welding protector as referred to in this specification can be a welding helmet, a welding shield or welding goggles, for example.

The automatic darkening filter assembly comprises a housing that forms an opening, for example a window, in which a switchable light filter is arranged. The switchable light filter is typically configured such hat it can be electrically switched between a dark-state and a light-state. In the dark-state any light transmission through the switchable light filter is reduced relative to the light-state. In the light-state the transmittance of the darkening filter may be within a range of about 1% to about 20%, in more particular within a range of about 5% to about 10%, whereas in the dark-state the transmittance of the darkening filter may be within a range of about 0,0005% to about 0.1%.

The switchable light filter is retained, or held in place, by a first and a second resilient gasket. The first and second gasket are arranged at least partially on opposite sides of the switchable light filter. The first and second gasket each extend circumferentially (in particular entirely circumferentially) adjacent a periphery of the switchable light filter. In particular, the switchable light filter typically has two opposite major surfaces, an eye facing surface and a welding arc facing surface. The eye facing surface forms an eye facing side of the switchable light filter and the welding arc surface forms a welding arc side of the switchable light filter. Hence, the eye facing surface and the welding arc surface form the opposite sides of the welding filter.

The first gasket may be at least partially arranged on the eye facing surface and the second gasket may be arranged at least partially on the welding arc facing surface of the switchable light filter. Preferably, at least a portion of the first gasket extends (preferably entirely) circumferentially on a margin of the eye facing surface of the switchable light filter, and at least a portion of the second gasket extends (preferably entirely) circumferentially on a margin of the welding arc facing surface of the switchable light filter.

The invention is advantageous in that it facilitates the assembly of the automatic darkening filter assembly. Further, the invention is advantageous in that it helps maximizing the mechanical shock resistance of the automatic darkening filter assembly or a welding protector using the automatic darkening filter assembly. For example, damages of the switchable light filter from ungentle handling or dropping of the automatic darkening filter assembly or the welding protector are minimized. Furthermore, the invention helps maximizing the lifetime of the automatic darkening filter assembly in that the first and second gasket hinder dust and/or moisture in reaching the edges switchable light filter.

In an embodiment the switchable light filter is clamped or restrained between the first and the second gasket. In particular, the first and the second gasket with the switchable light filter arranged between may form a sandwich that is held under a tension by the housing. The tension is upheld by a compression of the first and second gasket.

In an embodiment the housing comprises a first and a second housing part. The first and the second gasket are preferably arranged between the first and the second housing part. The first and second housing part are preferably mounted to each other, for example by a snap or screw connection. Other connections are possible as appropriate. Preferably, first and second housing part overlap with the switchable light filter. This means that preferably at least a portion of the first housing part, at least a portion of the first gasket, a portion of the switchable filter, at least a portion of the second gasket and at least a portion of the second housing part in combination form a sandwich. In this sandwich the switchable light filter is held and thus provided with a mechanical support by the first and the second housing part.

In an embodiment the first gasket is fixedly attached to the first housing part and the second gasket is fixedly attached to the second housing part. The attachment between the first gasket and the first housing part may comprise a positive locking (or form-fit) and/or material bond, and the attachment between the second gasket and the second housing part may comprise a positive locking (or form-fit) and/or material bond. In particular, the attachment between the first and second gasket and the first and second housing part, respectively, may be obtainable by two-component injection molding. The injection molding material of the first and second gasket, on the one hand, and the injection molding material of the first and second housing part, on the other hand, may be selected such that the material bond is automatically created during the two-component injection molding. For example, the first and second gasket may be made of a thermoplastic elastomer, of a type based on SBS (styrene butadiene styrene) and SEBS (styrene ethylene butylene styrene) and the first and second housing part may be made of polyamide. The polyamide is preferably molded first and overmolded by the thermoplastic elastomer. Thus, the material bond between the two injection molding materials can be achieved.

To provide additional mechanical strength and to hinder the first and second housing part to deform under tension over time, the polyamide may be provided with a glass fiber filler.

In an embodiment the first and second gasket exhibit a hardness of between 10 shore A and 50 shore A, more preferably between 30 shore A and 40 shore A and most preferably about 40 shore A. The shore hardness is typically provided by the injection molding material used for molding the first and second gasket. Preferably the first and second gasket are substantially nonporous. Thus, the first and second gasket obtain the same or generally the same hardness as the material used for molding.

In one embodiment the first and second housing part in combination form a frame. The frame may have a generally U-shaped profile and may extend around an edge of the switchable light filter. Preferably the frame holds the switchable light filter therein by a clamp fit via compression of the first and second gasket. Thus, slight relative movements of the switchable light filter and the housing are enabled, for example movements resulting from different thermal expansion of different material, while the switchable light filter is otherwise securely retained against movements. This minimizes the risk of damages (for example cracks) from high tensions that may arise between the switchable light filter and the housing).

In an embodiment the switchable light filter is curved. This means that preferably the eye facing surface and the welding arc facing surface correspond to portions of a cylinder shape. Further, the eye facing surface and the welding arc facing surface are preferably concentric. The radius of the cylinder shape may be within a range of 70 mm to 150 mm, more preferably within a range of 80 mm to 100 mm, most preferably 85 mm or about 85 mm. In this regard the radius refers to a mean radius between the eye facing surface and the welding arc facing surface.

In an embodiment the switchable light filter comprises a liquid crystal cell which has two transparent (preferably substantially colorless) substrates that each comprise a transparent electrode layer and an alignment layer for the liquid crystal molecules. The two transparent substrates are preferably made of glass. This provides for a high temperature stability and hermetic encapsulation of the liquid crystals. The switchable light filter further preferably has at least two polarizers that are arranged with their polarization directions oriented angularly offset to each other. Preferably, the switchable light filter further has at least two liquid crystal cells and three polarizers.

In an embodiment the automatic darkening filter assembly may further comprise electronic circuitry and one or more light sensors, for example photodetectors. The electronic circuitry is preferably configured to cause the liquid crystal cells to switch between the dark-state and the light-state dependent on light recognized by the light sensor(s). In particular, the electronic circuitry is preferably configured to cause the liquid crystal cells to switch in the dark-state upon the light sensor(s) detecting light above a predetermined light intensity, and to cause the liquid crystal cells to switch in the light-state otherwise. Thus, in case the light sensor(s) do not detect light above a predetermined light intensity, the electronic circuitry switches the liquid crystal cell to the light-state. Accordingly, the light-state is preferably the default state. This allows a welder to see through the automatic darkening filter assembly under normal light conditions. At the same time the welder is automatically protected from the exposure of harmful light intensities, for example from a welding arc.

In one embodiment the automatic darkening filter assembly is mounted in a welding shield of a welding protector. For example, the welding protector may have a window in which the automatic darkening filter assembly can be (exchangeably) retained. In another embodiment the first or the second housing part may form a welding shield.

Further disclosed is a welding protector which has a welding shield with a window in which a switchable light filter is arranged. The switchable light filter is smaller than the window. A circumferential gap between the switchable light filter and the window of the welding shield is closed by a resilient collar. The resilient collar is made of an elastic material, for example a rubber material or a thermoplastic elastomer as mentioned above.

The collar may have an outer retention structure for retaining the collar within the window of the welding shield. The collar may further have an inner retention structure for retaining the switchable light filter within the collar. The outer retention structure may, for example, form a groove for engaging with an edge of the welding shield that forms the window, and the inner retention structure may, for example, form a groove for engaging with an edge of the switchable light filter. The collar preferably has a generally flat ring-shaped portion connecting the outer and inner retention structure with each other. Due to the flat ring-shaped portion deformations of the welding shield or shocks of the welding shield are not transmitted to the switchable light filter or are dampened significantly. Thus the switchable light filter is protected from mechanical forces that may be exerted on the welding shield.

DETAILED DESCRIPTION OF THE INVENTION

Figure 1:
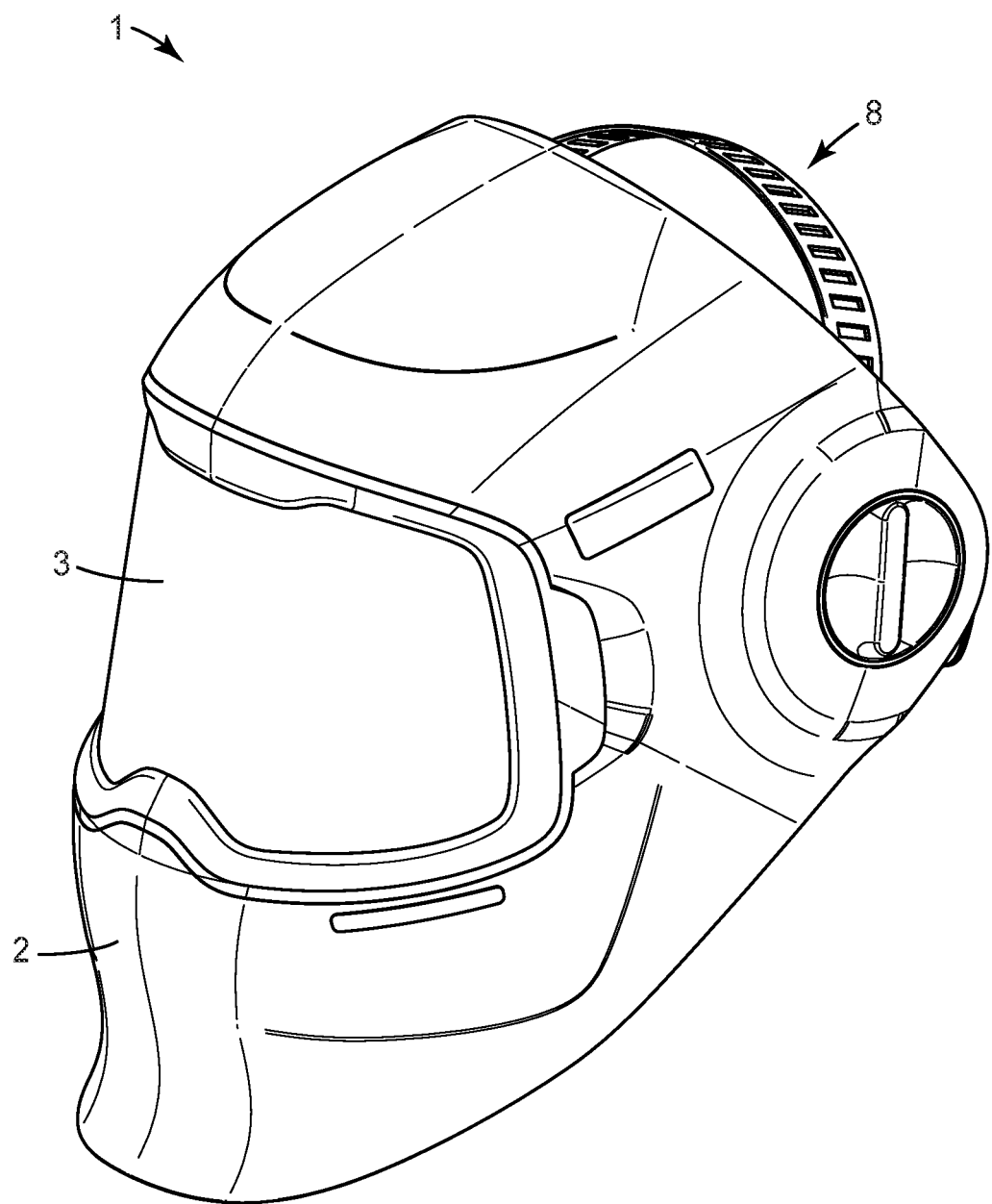
FIG. 1 is a perspective view of a welding protector, in particular a welding helmet, according to an embodiment of the invention.

FIG. 1 shows a welding protector 1 which in the example is a welding helmet. The invention is however not limited to a use with a welding helmet, but may likewise be used with a welding shield or welding goggles in an appropriate configuration.

The welding protector 1 has a protective shield portion 2 for protecting a welder's face (and other head portions) from radiation, dust and splashes of hot materials as these may occur during welding. The welding protector 1 further has an automatic darkening filter assembly 3 through which the welder can observe the welding arc during welding. In the example the automatic darkening is based on two liquid crystal cells by which the automatic darkening filter assembly 3 is electrically switchable between a light-state and a dark-state. When switched in the dark-state, the automatic darkening filter assembly 3 blocks a significant amount of light from being transmitted therethrough. This enables a user to observe a welding arc by seeing through the automatic darkening filter assembly 3 without risking to be exposed to harmful light radiation from the welding arc. In the light-state the automatic darkening filter assembly 3 permits a significant amount of light to be transmitted therethrough. Thus, the automatic darkening filter assembly 3 in the light-state allows the user to see under ambient light conditions (in the absence of the welding arc).

The automatic darkening filter typically comprises two or more liquid crystal cells that are arranged optically in sequence. This provides for multiplying the darkening effect (in the dark state) and thus a sufficient eye protection from light radiation. Further, the automatic darkening filter typically comprises one or more light sensors and electronic circuitry that causes the liquid crystal cells to switch dependent on light recognized by the light sensor(s).

Figure 2:
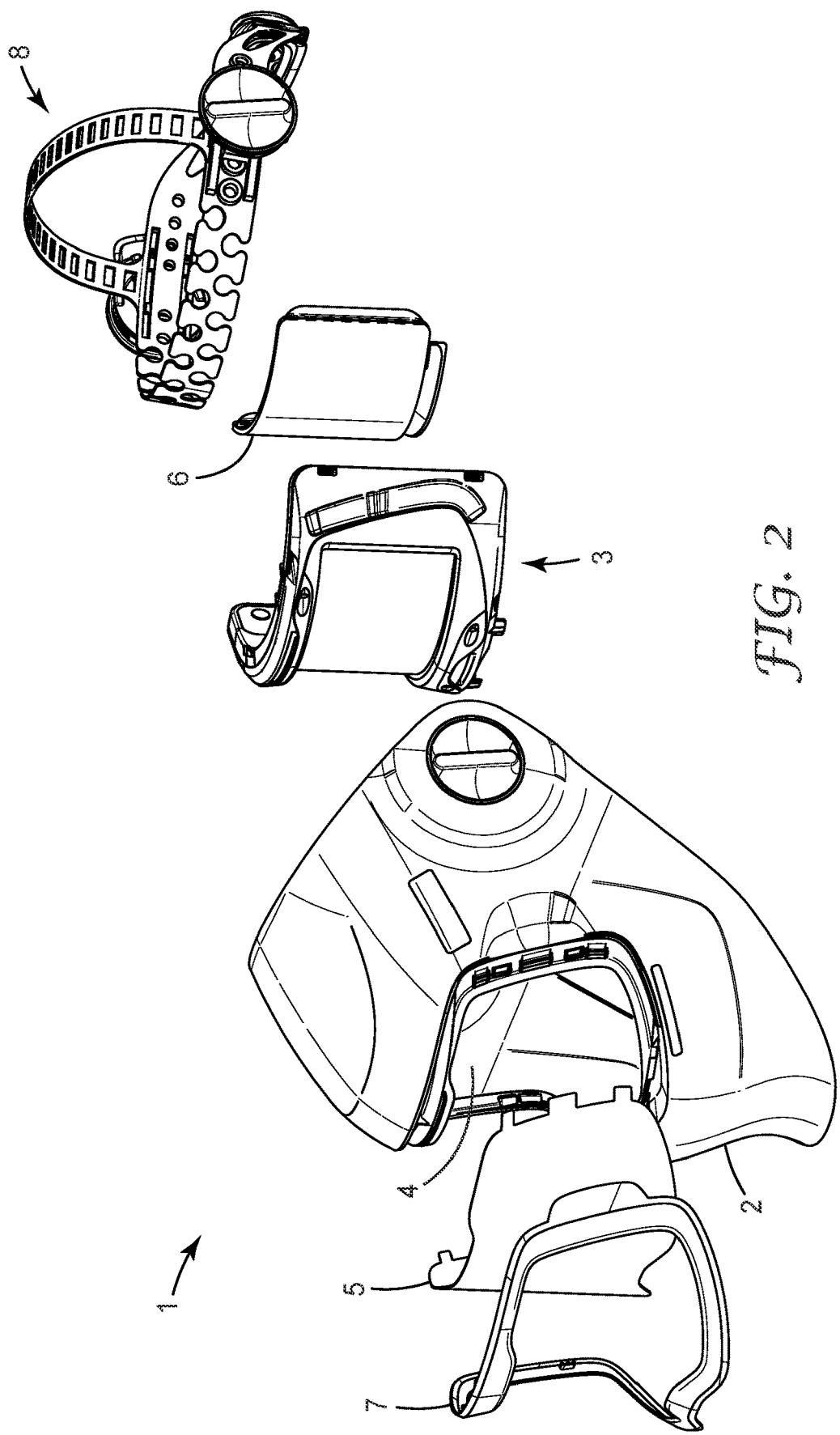
FIG. 2 is an exploded view of the welding protector shown in FIG. 1.

FIG. 2 shows the welding protector 1 in an exploded view. It is noted that the exploded view is a type of illustration only and that certain components that appear to be spaced from each other are normally mounted in contact to each other as shown in FIG. 1. The automatic darkening filter assembly 3 is mounted in a window 4 of the protective shield portion 2. Further, the welding protector 1 has a welding-arc-facing protective cover 5 and an eye-facing protective cover 6. These protective covers 5, 6 prevent dust and splashes of molten or hot material from directly reaching the automatic darkening filter assembly 3 and thus provide for protecting the automatic darkening filter assembly 3 from damages. These protective covers 5, 6 may be exchangeable. Therefore, any damages from dust or splashes of molten or hot material may occur on the protective covers 5, 6 which are typically less expensive than the automatic darkening filter assembly 3. The welding protector 1 in the example further has a cover frame 7 for closing any gaps between the protective shield 2 and the cover frame and/or the automatic darkening filter assembly 3. In the example, the welding protector 1 further has a headband arrangement 8 for fixing the welding protector 1 on the welder's head.

Figure 3:
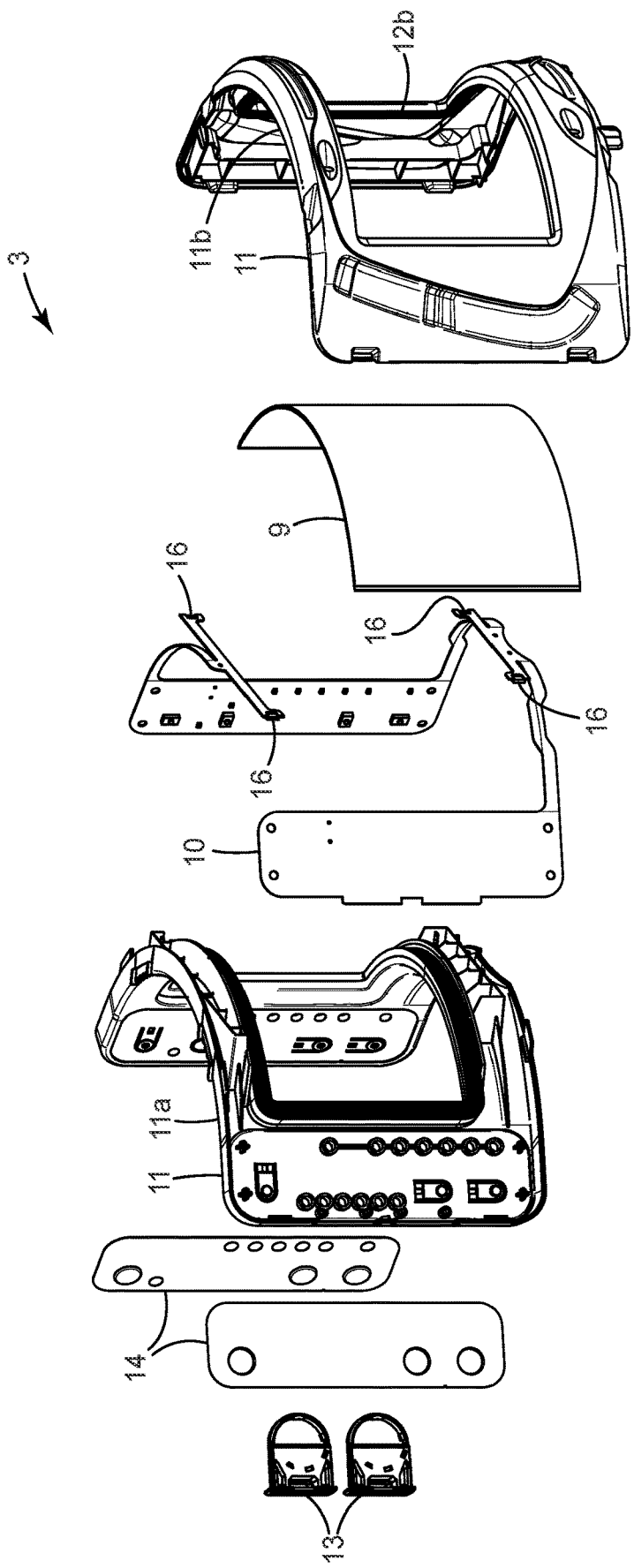
FIG. 3 is an exploded view of an automatic darkening filter assembly according to an embodiment of the invention.

FIG. 3 shows the automatic darkening filter assembly 3 in more detail. The automatic darkening filter assembly 3 has a switchable light filter 9. Although not illustrated in detail, the switchable light filter 9 comprises two liquid crystal cells (as mentioned). Each liquid crystal cell has two transparent substrates. In the example the transparent substrates are glass substrates. Each transparent substrate comprises a transparent electrode layer, in particular an indium tin oxide (ITO) layer, disposed on the transparent substrate, and an alignment layer disposed on the electrode layer. Between the transparent substrates a liquid crystal is disposed in direct contact with the alignment layers of the transparent substrates. On each transparent substrate a polarizer is disposed at the side opposite of the electrode and alignment layer. The alignment layers are arranged to orient the liquid crystal molecules in a determined direction when no voltage is applied to the electrode layers. Further, the polarizers are arranged such that in absence of the voltage light can pass through the liquid crystal cell. The second liquid crystal cell (of the same type as described) is arranged with one side on one of the polarizers and carries a third polarizer on the opposite side. Thus, the switchable light filter 9 has two liquid crystal cells and three polarizers. The third polarizer is arranged such that light can pass through the switchable light filter 9 in absence of a voltage applied to the electrode layers of the liquid crystal cells. Typically the switchable light filter 9 has at least one further permanent (not switchable) light filter, for example a UV light filter. The automatic darkening filter assembly 3 has an overall curved configuration and includes two curved two liquid crystal cells. Thus, a maximized field of vision is provided for the welder.

The automatic darkening filter assembly 3 further has a printed circuit board 10 which comprises electronic circuitry (including light sensors 16) for switching the switchable light filter 9. The printed circuit board 10 has controls, in particular push buttons, by which the automatic darkening filter assembly can be operated by a user. For example, the automatic darkening filter assembly 3 comprises a button for activating the automatic switching between the dark-state and the light-state. Other buttons may be provided, for example one or more buttons for adjusting the light transmission level in the dark state. In this regard it is noted that in the dark-state the light transmission through the automatic darkening filter 3 is reduced only (and not entirely blocked) so that a welder can observe a welding arc but at (significantly) reduced brightness. The adjustment of the light transmission level in the dark state allows an adaptation to welding arcs of different light intensities, for example due to different welding techniques or welding applications. Thus, the welding protector can be used for a variety of different welding techniques and applications, including autogenous welding.

Furthermore, the automatic darkening filter assembly 3 has a housing 11 having a first housing part 11a and a second housing part 11b. The first and second housing part 11a, 11b are mounted to form a frame for holding the switchable light filter 9. The housing 11 further provides a space for receiving the printed circuit board and a power supply, for example a battery. The first housing part 11a and the second housing part 11b each are provided with a first gasket 12a and a second gasket 12b. The first and second gasket 12a, 12b in the example are made of a thermoplastic elastomer, preferably a thermoplastic elastomer based on SBS (styrene butadiene styrene) and SEBS (styrene ethylene butylene styrene), having a shore A hardness of about 40. The housing 11 (in particular the first and second housing part 11a, 11b is made of a fiber reinforced polyamide. The first housing part 11a and the first gasket 12a as well as the second housing part 11b and the second gasket 12b are made by two-component injection molding. This means that the first housing part 11a is injection molded first and the first gasket 12a is injection molded directly on the first housing part 11a. Likewise the second housing part 11b is injection molded first and the second gasket 12b is injection molded directly on the second housing part 11b. Thus, the first and second gasket 12a, 12b are tightly attached to the first and second housing part 11a, 11b, respectively.

The automatic darkening filter assembly 3 in the example further has two inserts 13, each for a button cell battery. The skilled person will recognize that one or more batteries may be integrated in the automatic darkening filter assembly 3 by other means. For example, the battery or batteries may be accommodated in a receptacle or may be built in. Further, other types of a battery may be used.

The automatic darkening filter assembly 3 in the example further has labels 14 for marking any controls (for example push buttons) for operating the automatic darkening filter assembly 3. Further, the labels 14 may have instructions for a user, for example, instruction about an adjustment of the light transmission level in the dark-state for particular welding applications.

The automatic darkening filter assembly 3 forms a self-contained assembly unit which can be used in different welding protectors, such as a welding helmet or a welding shield, for example.

Figure 4:
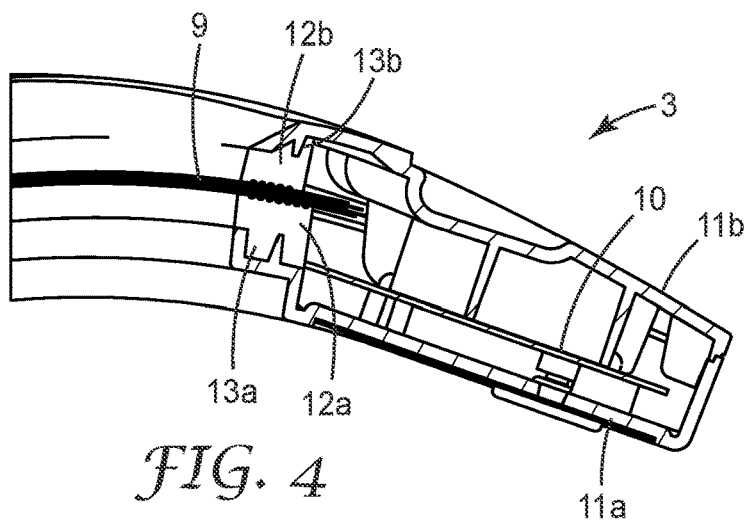
FIG. 4 is a cross-sectional partial view of an automatic darkening filter assembly according to an embodiment of the invention.

FIG. 4 shows a cross-section of a portion of the automatic darkening filter assembly 3. In particular, the first and second gasket 12a, 12b are retained at the first and second housing part 11a, 11b, respectively. In the example the first and second gasket 12a, 12b are retained at the first and second housing part 11a, 11b by material bond, in particular obtained by two-component injection molding. However, in the example the first and second gasket 12a, 12b are further retained at the first and second housing part 11a, 11b, respectively, by form-fit. The form-fit is provided by a first ridge 13a of the first gasket 12a, which engages a groove of the first housing part 11a, and further by a second ridge 13b of the second gasket 12b, which engages a groove of the second housing part 11b. Thus, the first and second gasket 12a, 12b are tightly fixed with the first and second housing part 11a, 11b, respectively. Thus certain deformations of the first and second housing part 11a, 11b can be compensated by the first and second gaskets 12a, 12b. Therefore the transmission of deformations from the first and second housing part 11a, 11b on the switchable light filter 9 can be minimized. Switchable light filters are therefore protected from such deformations. In particular switchable light filters which comprise glass-substrates may be prevented from breaking. Further, the relatively soft first and second gasket 12a, 12b provide shock absorbing properties so that the switchable light filter is also protect from shocks, for example due to handling or dropping of the welding protector. In the example the first gasket 12a has a rim 15a (visible in FIG. 5). The rim 15a at least partially (or entirely) surrounds the switchable light filter 9. Thus, the switchable light filter 9 is captured and held within the rim 15a. As shown the rim 15a cooperates with the second gasket 12b to provide an additional edge seal for the switchable light filter 9. Accordingly, dust and moisture are hindered in reaching the edge of the switchable light filter 9. Although the switchable light filter 9 has an edge seal that captures the liquid crystals within the liquid crystal cell, the additional edge seal provided by the first and second gasket help maximizing the lifetime of the switchable light filter 9.

Figure 5:
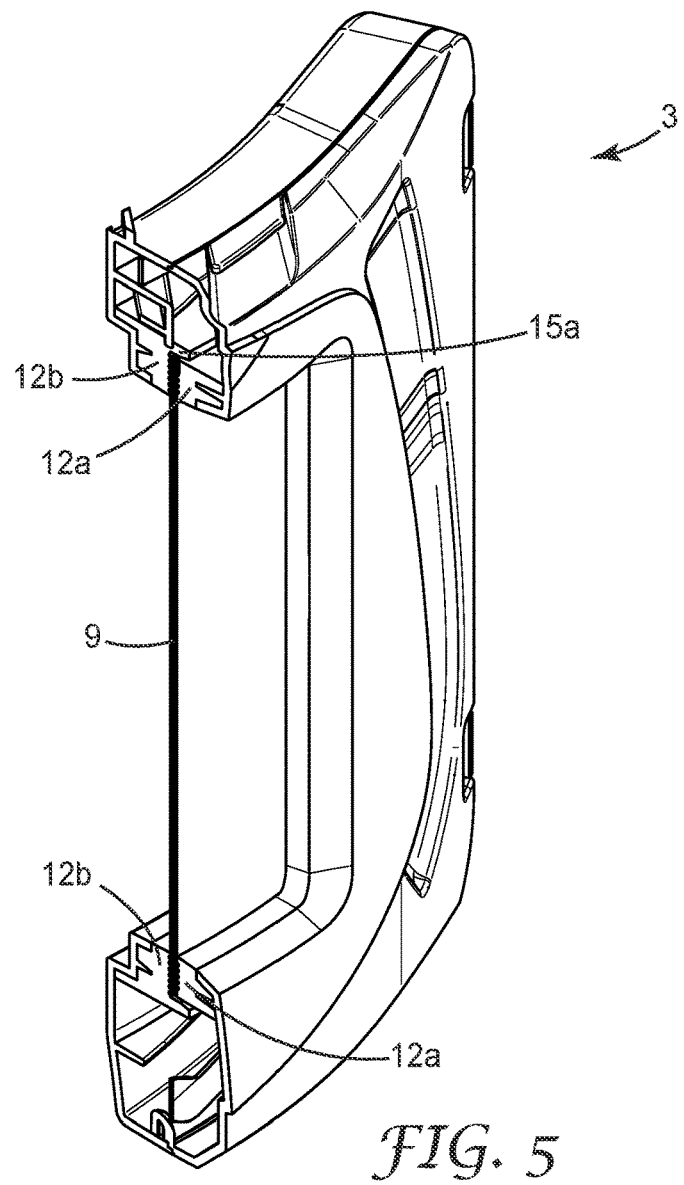
FIG. 5 is a further cross-sectional partial view of an automatic darkening filter assembly according to an embodiment of the invention.

FIG. 5 shows a further cross-section of a portion of the automatic darkening filter assembly 3. In the example the first gasket 12a has three circumferential ridges 14 and the second gasket 12b is generally flat. This provides the first gasket 12a with a somewhat greater resilience relative to the second gasket 12b. Thus, the switchable light filter 9 is circumferentially clamped by the first and second gasket 12a, 12b. Further, the clamping force is relatively uniform along the circumference the first and second gasket 12a, 12b due to the ridges provided at the first gasket. It is noted that likewise instead of three ridges one, two or more than three ridges may be provided at the first and or the second seal.

Figure 6A:
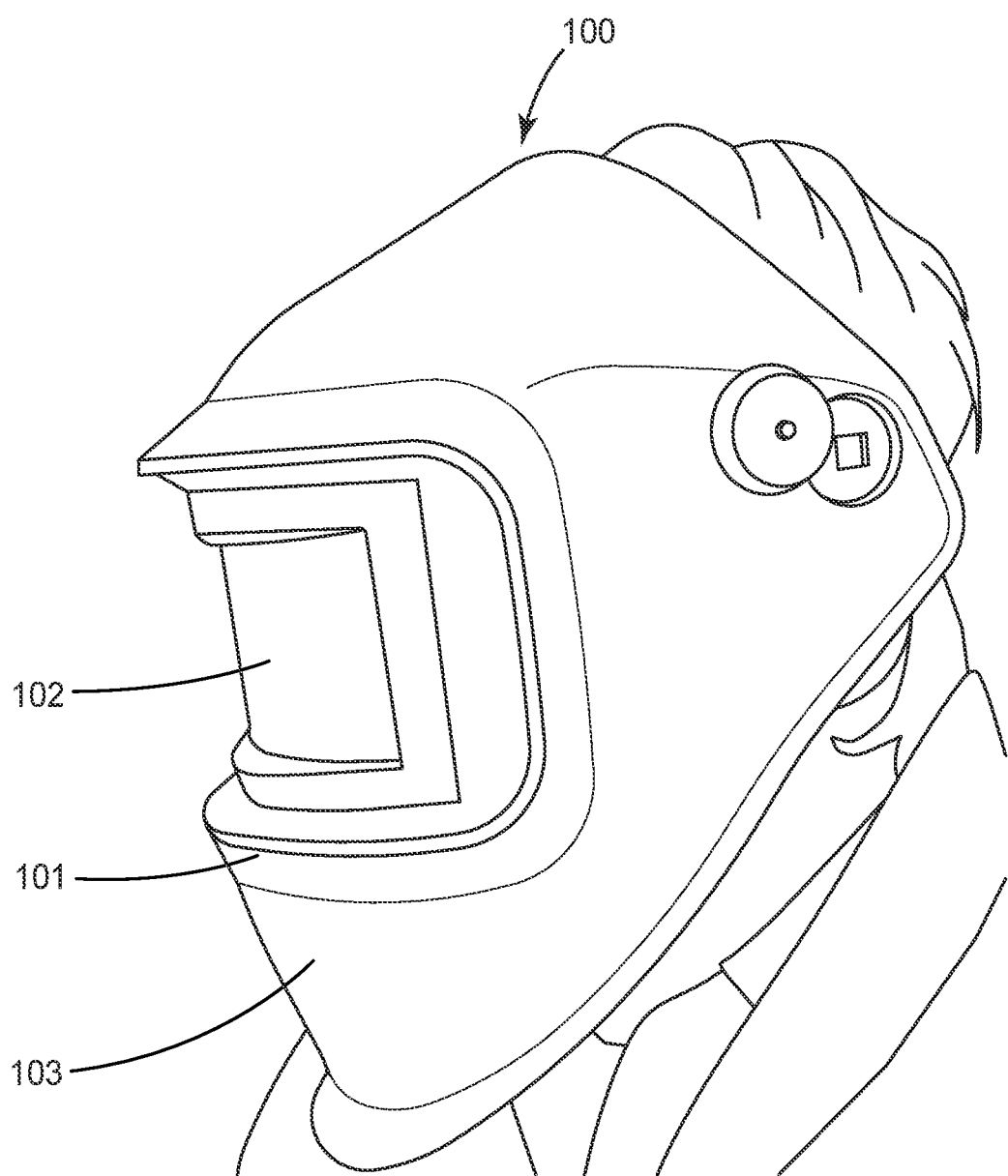
FIG. 6A is a photo of a welding helmet.

FIG. 6A shows a welding protector 100 which has welding shield 103 in which a switchable light filter 102 is arranged. A resilient collar 101 is arranged in a circumferential gap between the switchable light filter 102 and the welding shield 103 so that the switchable light filter 102 is not directly in contact with the welding shield 103.

Figure 7A:
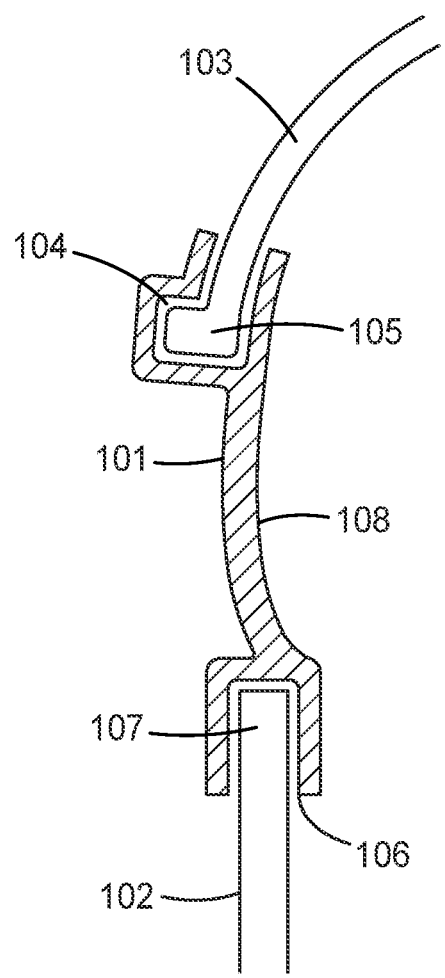
FIG. 7A is a cross-sectional view of the helmet shown in FIG. 6A.

As shown in FIG. 7A the collar has a groove 104 for engaging with an edge 105 of the welding shield 103. The edge 105 of the welding shield 103 forms a window in the welding shield. The collar 101 further has a groove 106 for engaging with an edge 107 of the switchable light filter 102. The switchable light filter 102 may be furnished with further filters, for example polarizers, UV and/or IR filters, for example. The collar has a generally flat ring-shaped portion 108 which connecting the portions of the collar 101 that form the grooves 104, 106 with each other. The flat ring-shaped portion mechanically decouples the welding shield 103 from the switchable light filter 102. Thus, the switchable light filter is protected from mechanical forces that may be exerted on the welding shield.

The invention claimed is:

1. An automatic darkening filter assembly for a welding protector, comprising a housing that forms an opening in which a curved switchable light filter is arranged, wherein the curved switchable light filter is contacted and retained by a first and a second resilient gasket that are arranged on opposite sides of the curved switchable light filter and which each extend circumferentially adjacent a periphery of the curved switchable light filter.

2. The automatic darkening filter assembly of claim 1, wherein the curved switchable light filter is clamped between the first and the second gasket.

3. The automatic darkening filter assembly of claim 1, wherein the housing comprises a first and a second housing part and wherein the first and the second gasket are arranged between the first and the second housing part.

4. The automatic darkening filter assembly of claim 1, wherein the first gasket is fixedly attached to the first housing part and wherein the second gasket is fixedly attached to the second housing part.

5. The automatic darkening filter assembly of claim 4, wherein the attachment between the first and second gasket and the first and the second housing part, respectively, comprises a positive locking and/or material bond.

6. The automatic darkening filter assembly of claim 4, wherein the attachment between the first and second gasket and the first and the second housing part, respectively, is obtainable by two-component injection molding.

7. The automatic darkening filter assembly of claim 1, wherein the first and second gasket exhibit a hardness of between 10 shore A and 50 shore A.

8. The automatic darkening filter assembly of claim 1, wherein the first and second gasket are made of a thermoplastic elastomer.

9. The automatic darkening filter assembly of claim 3, wherein the first and second housing part in combination form a frame that holds the curved switchable light filter therein by a clamp fit via compression of the first and second gasket.

10. The automatic darkening filter assembly of claim 1, wherein the first resilient gasket includes a rim that at least partially surrounds the curved switchable light filter.

11. The automatic darkening filter assembly of claim 1, wherein the curved switchable light filter comprises a liquid crystal cell which has two transparent substrates that each comprise a transparent electrode layer and an alignment layer for the liquid crystal molecules.

12. The automatic darkening filter assembly of claim 11, wherein the curved switchable light filter further has at least two polarizers that are arranged with their polarization directions oriented angularly offset to each other.

13. The automatic darkening filter assembly of claim 12, wherein the curved switchable light filter further at least two liquid crystal cells and three polarizers.

14. A welding protector comprising the automatic darkening filter assembly according to claim 1.

15. The welding protector of claim 14, wherein the automatic darkening filter assembly is mounted in a welding shield of the welding protector.

16. The automatic darkening filter assembly of claim 10, wherein the rim cooperates with the second resilient gasket to provide an edge seal for the curved switchable light filter.

17. The automatic darkening filter assembly of claim 1, wherein the first resilient gasket includes a plurality of circumferential ridges.

\* \* \* \* \*